US011031126B1

(12) United States Patent
Caudill

(10) Patent No.: US 11,031,126 B1
(45) Date of Patent: Jun. 8, 2021

(54) MEDICAL THERAPY SYSTEMS WITH CLOSED-LOOP CONTROLS AND METHODS OF MAKING AND USING THE SAME

(71) Applicant: Mast Medical Systems, Inc., San Francisco, CA (US)

(72) Inventor: Charles Harrison Benton Caudill, San Francisco, CA (US)

(73) Assignee: Mast Medical Systems, Inc., San Francisco, CA (US)

( * ) Notice: Subject to any disclaimer, the term of this patent is extended or adjusted under 35 U.S.C. 154(b) by 0 days.

(21) Appl. No.: 16/886,723

(22) Filed: May 28, 2020

Related U.S. Application Data

(60) Provisional application No. 63/024,197, filed on May 13, 2020, provisional application No. 63/003,964, filed on Apr. 2, 2020.

(51) Int. Cl.
*G16H 40/60* (2018.01)
*A61M 5/172* (2006.01)
*A61M 5/142* (2006.01)

(52) U.S. Cl.
CPC .......... *G16H 40/60* (2018.01); *A61M 5/1723* (2013.01); *A61M 2005/14208* (2013.01); *A61M 2205/3327* (2013.01); *A61M 2205/52* (2013.01)

(58) Field of Classification Search
CPC ...... A61M 5/1723; A61M 2005/14208; A61M 2005/3327; A61M 2205/52;
(Continued)

(56) References Cited

U.S. PATENT DOCUMENTS 5,101,820 A 4/1992 Christopher
6,158,430 A 12/2000 Pfeiffer
(Continued)

FOREIGN PATENT DOCUMENTS

FR 863412 4/1941
WO WO-2012140136 10/2012

OTHER PUBLICATIONS

U.S. Appl. No. 16/882,428, filed May 22, 2020, Caudill.
(Continued)

*Primary Examiner* — Manuel A Mendez
(74) *Attorney, Agent, or Firm* — Perkins Coie LLP

(57) ABSTRACT

A closed-loop control for a medical therapeutic system is disclosed that includes one or more processes or components for/in the medical therapeutic system, a controller configured to determine whether one or more operations of the process(es) or component(s) are within a corresponding safety envelope, and one or more sensors. The process(es)/component(s) are configured to deliver a controlled amount of a substance, energy or force to a patient. The sensor(s) are configured to measure or determine a value of a measurable parameter of the process(es)/component(s) and/or effected by the operation(s), and provide the value(s) of the measurable parameter(s) to the controller. The controller determines whether each of the operation(s) are within the corresponding safety envelope according to a corresponding function that mathematically describes the operation. The safety envelope corresponds to known safe values of the measurable parameter, or an unmeasured parameter based on the measurable parameter.

19 Claims, 5 Drawing Sheets

(58) Field of Classification Search
CPC ............ A61B 17/320092; A61B 34/25; A61B 17/320068; A61B 5/0022; A61B 5/14532; A61B 5/1495; G16H 20/17; G16H 40/63; G16H 40/67; G16H 40/60; G06Q 10/10
See application file for complete search history.

(56) References Cited

U.S. PATENT DOCUMENTS

| | | |
|---|---|---|
| 10,007,238 B1 | 6/2018 | Taube |
| 2005/0085799 A1 | 4/2005 | Luria et al. |
| 2011/0197884 A1 | 8/2011 | Duff |
| 2012/0059351 A1* | 3/2012 | Nordh ................ A61M 5/1723 604/503 |
| 2013/0306062 A1 | 11/2013 | Larson |
| 2015/0190577 A1* | 7/2015 | Shaanan ........... A61M 5/31585 604/66 |

OTHER PUBLICATIONS

Gomes et al., "Formal Specification of Cardiac Pacing System," A. Cavalcanti and D. Dams, 2006, 16 pages.
Pajic et al., "Model-Driven Safety Analysis of Closed-Loop Medical Systems," IEEE Transactions of Industrial Informatics, Oct. 2012, 13 pages.

* cited by examiner

MEDICAL THERAPY SYSTEMS WITH CLOSED-LOOP CONTROLS AND METHODS OF MAKING AND USING THE SAME

RELATED APPLICATION(S)

This application claims priority to U.S. Provisional Pat. Appl. Nos. 63/003,964 and 63/024,197, respectively filed on Apr. 2, 2020 and May 13, 2020, each of which is incorporated herein by reference.

FIELD OF THE INVENTION

The present invention generally relates to the field of medical therapy systems with closed-loop controls.

DISCUSSION OF THE BACKGROUND

Many medical devices are compact systems that provide continuous and/or as-needed therapies to patients. Such devices and the patients receiving treatment therefrom benefit from a control system.

A closed-loop control system comprises a set of devices or other hardware that, in conjunction with appropriate software, automatically regulates a process variable to a desired state or set point without human interaction. Closed-loop control systems contrast with open-loop control systems, which require manual input.

A control loop is a system or subsystem of hardware components and software control functions involved in measuring and adjusting a variable that controls a particular process. Closed loop control systems are widely used in various applications, including agriculture, chemical plants, quality control, nuclear power plants, water treatment plants and environmental control. However, many medical devices lack closed-loop controls.

An insulin pump is an electromechanical device that subcutaneously delivers insulin to a patient, both at preset continuous basal rates and in extra bolus doses at mealtimes on demand. FIG. 1 shows a block diagram for a conventional insulin pump 100, including a reservoir 110, a pump 120, and an infusion set or needle assembly 130. The conventional insulin pump 100 also includes a controller 140, receiving power from a power supply 150, and receiving patient blood glucose data from a blood sensor 160. FIG. 2 shows the physical components of a conventional insulin pump 200, including a cartridge (reservoir) 210, an adapter 220 for connecting a Teflon cannula/needle to the cartridge, a plunger 230, a drive nut 240 and piston rod 245 configured to drive the plunger 230 in the cartridge 210, a motor and gear 250 that operates the drive nut 240 and piston 245, a display 260, a plurality of on/off operating buttons 270, and one or more batteries 280a-b that provides electrical power to those components needing it. The reservoir/cartridge 210, which is similar to a syringe, holds a 2- to 3-day supply of insulin and is placed into (or in operative communication with) the battery-powered pump. The infusion set 290 includes tubing 292 that connects the reservoir 210 to a cannula 294 (i.e., a tiny tube to deliver insulin subcutaneously), and transports the insulin from the reservoir to the patient. A small piece of adhesive 296 may hold the cannula 294 in place at the insertion site.

Patients and medical professionals in the field of diabetes treatment have increasingly demanded closed-loop controls in insulin therapy. There is a concern that the lack of closed-loop control systems in some insulin therapy systems, such as insulin pumps, may have led to more emergency treatments and deaths from poor sugar control than would have resulted from conventional patient self-administration of insulin and patient-monitored blood testing in patients treated with such insulin therapy systems.

FIG. 3 is a diagram providing an overview of a conventional medical ventilator system 300. The conventional ventilator system includes an air pump 310, an air conditioner 320, a source (e.g., tank) of oxygen 330, a filter 340, a plurality of sensors 350, a user interface 360, and a system control subunit 370. The physician inputs information and control settings into the user interface 360. Oxygen or a mixture of oxygen and one or more other gases (e.g., nitrogen, air, etc.) is provided from the oxygen source 330 to the air conditioner 320. The oxygen (or separately-supplied air) may pass through the filter 340 prior to conditioning in the air conditioner 320. The air conditioner 320 may adjust or modify one or more parameters of the oxygen and/or air, such as temperature, humidity, oxygen content (e.g., percentage), etc. The air pump 310 then provides the conditioned air to the patient, typically through a tube. The sensors 350 receive samples (e.g., of exhaled air) or information (such as pulse rate) from the patient and from the ventilator unit 300, measure certain parameters of the samples (e.g., in the case of the patient, oxygen content and/or carbon dioxide content; in the case of the ventilator, the pressure of the oxygen provided to the patient through the tube), and feed back the measurements and information to the system control subunit 370.

The system control subunit 370 displays some or all of the measurements and information on the user interface 360, and the physician or other medical professional sees the displayed measurements and/or information and makes medical decisions for the patient based thereon. However, current ventilators frequently lack a desired degree of autonomy, resulting in a disproportionate amount of physician-time per patient being spent to control and adjust settings on the ventilator.

Formal methods for developing control systems exist in the areas of model verification and verified software monitors. A typical application of such formal methods involves developing a model, reasoning about critical properties, and then synthesizing an implementation from the model. Tools exist that can determine whether the implementation matches the verified model. However, such formal methods for development of control systems take time to implement, execute and optimize.

This "Discussion of the Background" section is provided for background information only. The statements in this "Discussion of the Background" are not an admission that the subject matter disclosed in this "Discussion of the Background" section constitutes prior art to the present disclosure, and no part of this "Discussion of the Background" section may be used as an admission that any part of this application, including this "Discussion of the Background" section, constitutes prior art to the present disclosure.

SUMMARY OF THE INVENTION

The present invention relates to medical therapy systems, and more specifically, to medical therapy systems having one or more closed-loop control subsystems, and methods of making and using such medical therapy systems.

In one aspect, the present invention relates to a closed-loop control for a medical therapeutic system, comprising one or more processes or components for or in the medical therapeutic system, a controller, and one or more sensors.

The processes or components are configured to deliver a controlled amount of a substance, an energy or a force to a patient in need thereof. The controller is configured to determine whether one or more operations of the process(es) or component(s) are within a corresponding predefined safety envelope. Each of the sensors is configured to measure or determine a value of a measurable parameter (1) of the process(es) or component(s) and/or (2) effected by the operation(s) of the process(es) or component(s), and provide the value(s) of the measurable parameter(s) to the controller. The controller determines whether each of the operation(s) of the process(es) or component(s) are within the corresponding predefined safety envelope according to a corresponding function that describes mathematically the operation of the process(es) or component(s). The predefined safety envelope corresponds to known safe values of (1) the measurable parameter or (2) an unmeasured parameter based on the measurable parameter.

The medical therapy system may include an insulin pump, a ventilator system, a continuous positive airway pressure (CPAP) machine, a laser therapy system (e.g., for keratotomy, cataract removal, tattoo removal, etc.), angiography and other coronary therapies (e.g., pacemakers, defibrillators), radiation therapy, etc. The medical therapy system can also include diagnostic systems, such as X-ray radiography equipment, magnetic resonance imagers, positron emission tomography (PET) scanners, computed tomography (CT) scanners, etc.

In some embodiments, the controller includes a physical memory containing non-transitory, executable code. In other or further embodiments, the function that describes mathematically the corresponding operation of the process(es) or component(s) comprises a model of the corresponding operation of the process(es) or component(s), and/or the predefined safety envelope comprises one or more mathematical descriptions of maximum or minimum limits for the measurable parameter or the unmeasured parameter. For example, the predefined safety envelope may comprise mathematical descriptions of the maximum limit and the minimum limit for the unmeasured parameter.

In various embodiments, the process(es) or component(s) comprise first and second processes or components, the controller includes a physical memory containing non-transitory, executable code, the function that describes mathematically the corresponding operation comprises a model of the corresponding operation of the process or component, and the predefined safety envelope comprises one or more mathematical descriptions of maximum or minimum limits for the measurable parameter or the unmeasured parameter.

Some embodiments of the present closed-loop control are for multiple processes and/or components. For example, when the "one or more processes or components" comprise first and second processes or components, the "one or more sensors" comprise first and second sensors, and the controller determines whether the operations of each of the first and second processes or components are within corresponding first and second predefined safety envelopes according to first and second functions that respectively describe mathematically the corresponding operations of the first and second processes or components.

In other or further embodiments, each of the process(es) or component(s) are configured to provide to the controller one or more recommendations relating to the corresponding operation(s). The controller can accept such a recommendation when the corresponding operation(s) are or remain within the corresponding predefined safety envelope, but the controller must reject the recommendation when at least one of the corresponding operation(s) is outside the corresponding predefined safety envelope.

In some embodiments, the controller determines whether each of the operation(s) of the process(es) or component(s) are within the corresponding predefined safety envelope by calculating a value of an unmeasured parameter (1) of the process(es) or component(s) and/or (2) effected by the operation(s) of the process(es) or component(s) from the value(s) of the measurable parameter(s). This function of the controller can be applied to multiple unmeasured parameters, as well as to one or more measurable parameters.

The present closed-loop control can be part of a medical therapeutic system that further comprises a reservoir, chamber or vessel containing the substance (to be delivered to the patient) and a tube, conduit or other delivery mechanism through which the substance is delivered to the patient. Alternatively, the medical therapeutic system may further comprise a process or component configured to irradiate the patient with a controlled amount of energy (e.g., X-ray, ultraviolet, positron, or ultrasound radiation), or apply a controlled force (e.g., a mechanical or electromagnetic force) to the patient.

Another aspect of the present invention concerns a theorem-proven controller for a medical therapeutic system, comprising a microcontroller, microprocessor, a field programmable gate array (FPGA), or an application specific integrated circuit (ASIC), and a physical memory. The microcontroller, microprocessor, FPGA or ASIC is configured to execute instructions to determine whether one or more operations of one or more processes or components of the medical therapeutic system are within a corresponding predefined safety envelope according to one or more functions. Each of the function(s) corresponds to a unique one of the operation(s), and describes mathematically the corresponding operation. The physical memory contains non-transitory, executable code including the instructions, the function that describes mathematically the corresponding operation of the process(es) or component(s), and the predefined safety envelope. The function that mathematically describes the corresponding operation comprises a model of the corresponding operation of the process(es) or component(s). The predefined safety envelope comprises one or more mathematical descriptions of maximum or minimum limits for a measurable or unmeasured parameter of the process(es) or component(s) and/or effected by the operation(s) of the process(es) or component(s). The microcontroller, microprocessor, FPGA or ASIC is configured to (i) maintain the operation(s) of the process(es) or component(s) within the corresponding safety envelope(s) or (ii) alert a user of the medical therapeutic system when at least one of the operation(s) of the process(es) or component(s) is outside the corresponding safety envelope(s). The code is updatable and/or modifiable by iteration (i) of the operation(s) and/or (ii) with the medical therapeutic system.

In another aspect, the present invention relates to a method of generating a closed-loop control system for a medical therapeutic system, comprising building an architecture model from requirements for the medical therapy system, deriving (i) design models for the medical therapy system and/or for processes or components thereof and (ii) a function that describes mathematically one or more operations of the medical therapy system, the process(es) or the component(s), adding or inputting one or more control loops to the architecture and design models, determining whether the models comply with predefined constraints for the system, the process(es) or the component(s). The function includes one or more measurable parameters (1) of the system, process(es) or component(s) and/or (2) effected by the operation(s). The control loop(s) are configured to determine whether the operation(s), the process(es) or component(s) are within a corresponding predefined safety envelope according to the function. Determining whether the models comply with the predefined constraints is based on the function and the safety envelope(s). When at least one of the operations is outside the predefined safety envelope, the method comprises modifying one or more of the architecture and/or design models and/or one or more of the constraints, and determining again after the modification whether the models comply with the constraints. Typically, when all of the operations are within the predefined safety envelope, the method comprises downloading, installing, or embedding code generated from the architecture and/or design models, the safety envelope(s) and the constraints onto or in a controller in the medical therapy system. Some embodiments of the method concern a plurality of (e.g., first and second) processes or components, in which case the controller determines whether the operations of each of the first and second processes or components are within corresponding first and second predefined safety envelopes according to first and second functions that respectively describe mathematically the corresponding operations of the first and second processes or components.

In some embodiments, the method may further comprise determining that all of the operation(s) of the system, the process(es) or the component(s) are within the corresponding predefined safety envelope, after simulating the models under the constraints. In such embodiments, the code may be downloaded, installed, or embedded onto or in the controller after determining that all of the operation(s) of the system, the process(es) or the component(s) are within the corresponding predefined safety envelope.

In other or further embodiments of the method, the predefined safety envelope comprises one or more mathematical descriptions of maximum or minimum limits for a measurable parameter or an unmeasured parameter of and/or affected by the operation(s) of the process(es) or component(s). For example, the predefined safety envelope may comprise mathematical descriptions of the maximum limit and the minimum limit for the unmeasured parameter. In other or further embodiments, determining whether the models comply with the predefined constraints comprises (i) calculating a value of an unmeasured parameter (1) of the process(es) or component(s) and/or (2) affected by the operation(s) of the process(es) or component(s) from one or more values of a corresponding measurable parameter, and (ii) comparing the value of the unmeasured parameter with the corresponding safety envelope.

In some embodiments, each of the process(es) or component(s) are configured to provide a recommendation relating to the corresponding operation(s), and the model can accept the recommendation when the corresponding operation(s) of the process(es) or component(s) are within the corresponding predefined safety envelope, but the model must reject the recommendation when at least one of the corresponding operation(s) of the process(es) or component(s) is outside the corresponding predefined safety envelope. In such embodiments, the code generated from the architecture and/or design models is theorem-proven, but the control loop(s) are untrusted.

The advantages of the present invention will become readily apparent from the detailed description of various embodiments below.

DETAILED DESCRIPTION

Figure 1:
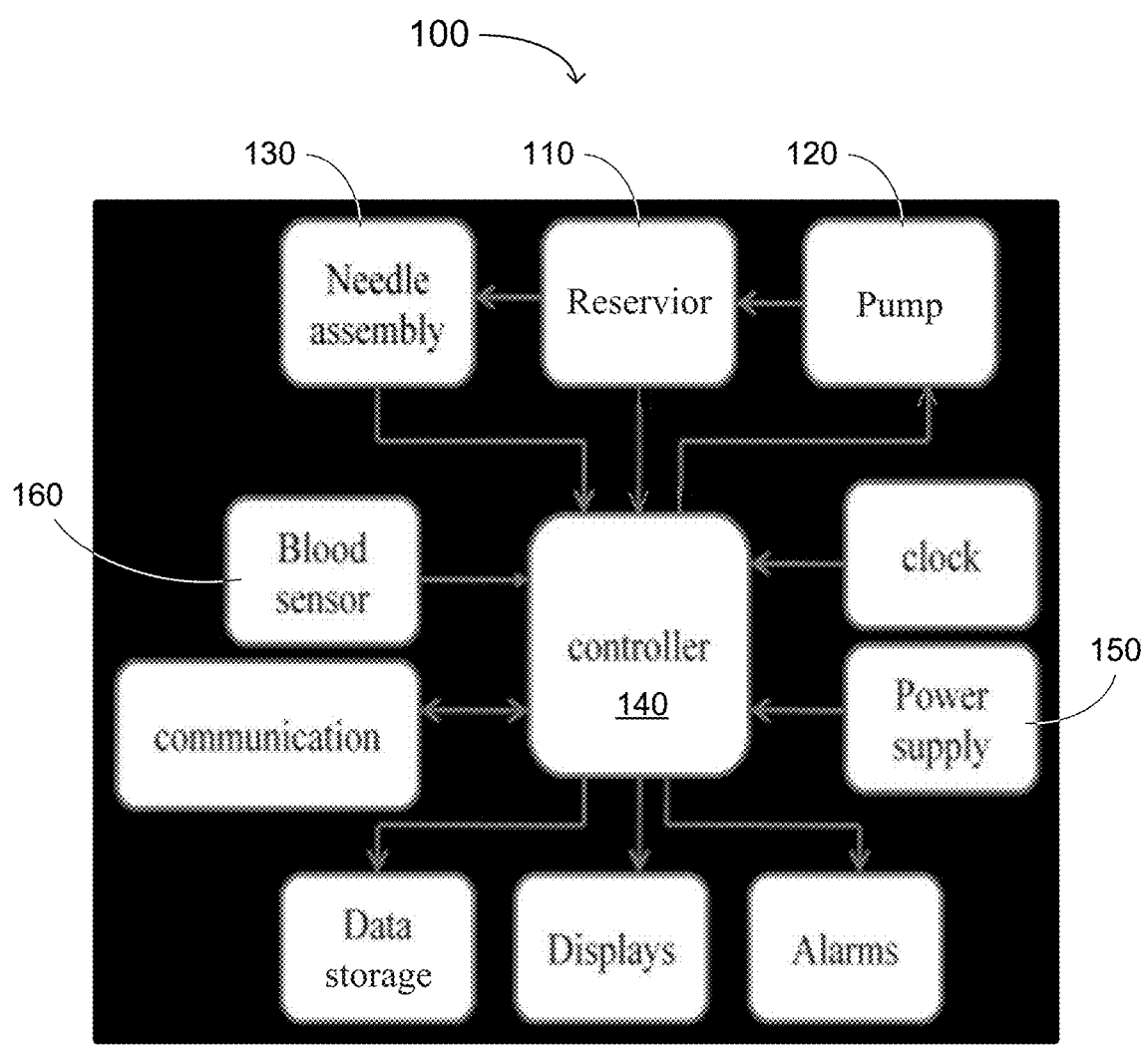
FIG. 1 is a diagram showing a block diagram for a conventional insulin pump.

Reference will now be made in detail to various embodiments of the invention, examples of which are illustrated in the accompanying drawings. While the invention will be described in conjunction with the following embodiments, it will be understood that the descriptions are not intended to limit the invention to these embodiments. On the contrary, the invention is intended to cover alternatives, modifications and equivalents that may be included within the spirit and scope of the invention. Furthermore, in the following detailed description, numerous specific details are set forth in order to provide a thorough understanding of the present invention. However, it will be readily apparent to one skilled in the art that the present invention may be practiced without these specific details. In other instances, well-known methods, procedures and components have not been described in detail so as not to unnecessarily obscure aspects of the present invention. Furthermore, it should be understood that the possible permutations and combinations described herein are not meant to limit the invention. Specifically, variations that are not inconsistent may be mixed and matched as desired.

The technical proposal(s) of embodiments of the present invention will be fully and clearly described in conjunction with the drawings in the following embodiments. It will be understood that the descriptions are not intended to limit the invention to these embodiments. Based on the described embodiments of the present invention, other embodiments can be obtained by one skilled in the art without creative contribution and are in the scope of legal protection given to the present invention.

Furthermore, all characteristics, measures or processes disclosed in this document, except characteristics and/or processes that are mutually exclusive, can be combined in any manner and in any combination possible. Any characteristic disclosed in the present specification, claims, Abstract and Figures can be replaced by other equivalent characteristics or characteristics with similar objectives, purposes and/or functions, unless specified otherwise.

For the sake of convenience and simplicity, the terms "therapeutic" and "therapy" are, in general, interchangeable and may be used interchangeably herein, but are generally given their art-recognized meanings. Wherever one such term is used, it also encompasses the other term. Similarly, for convenience and simplicity, the terms "control" and "control loop" may be used interchangeably herein, but are generally given their art-recognized meanings, and wherever one such term is used, it also encompasses the other terms. In addition, for convenience and simplicity, the terms "part," "portion," and "region" may be used interchangeably but these terms are also generally given their art-recognized meanings. Also, unless indicated otherwise from the context of its use herein, the terms "known," "fixed," "given," "certain" and "predetermined" generally refer to a value, quantity, parameter, constraint, condition, state, process, procedure, method, practice, or combination thereof that is, in theory, variable, but is typically set in advance and not varied thereafter when in use.

Herein, a "control loop" may refer to a loop of a computer-executed software program that reads a configured operational mode of the system and executes a prescribed or corresponding algorithm, whereas a "closed-loop control" is a control loop in which the operational mode is modifiable based upon feedback (e.g., from the system; e.g., when a sensor configured to monitor the operation or a parameter thereof or affected thereby provides measurement information to the controller, which in turn, can modify the operation to bring the parameter within defined limits or constraints). In addition, the term "measurable" refers to a parameter that can be measured, and in practice, typically is measured to provide data/information about the parameter or its value to the controller or control subsystem. The term "unmeasured" refers to a parameter that is not measured directly in the system, but that is calculated by the controller or control subsystem in practice, typically according to a mathematical formula, to obtain data/information about the parameter or its value.

Exemplary Methods of Demonstrating Patient Safety in a Medical Therapy System

In one aspect, the present invention employs theorem-proven models and/or safety envelopes to demonstrate patient safety in medical therapy systems. In one example, the medical therapy system is an insulin pump. In another, the medical therapy system is a medical ventilator unit.

To address safety and reliability concerns in modern medical therapy systems, targeted, practical methods of closed-loop control may be applied in the early design and implementation stages of the system. Typically, formal control methods are not well-suited for rapid prototyping and deployment of new or modified systems. However, there are some approaches that can significantly advance patient safety within relatively short time constraints.

For safety- or security-critical, physical, real-time control systems, there are unique challenges in the application of formal methods. Therefore, the present control method and system provide a series of modes of operation, given specific input parameters. For example, in a ventilator system, input parameters may include a respiratory rate, a tidal volume, gas pressure(s), gas temperature, a flow rate, an oxygen level (e.g., percentage of oxygen in the gas mixture supplied to the patient), humidity (e.g., of the gas mixture supplied to the patient), etc.

The present invention encompasses two approaches for closed-loop control in medical therapy systems, both of which can be at least partially based on currently available tools. A first approach involves developing models of critical discrete control code models. First, the correctness of the model is verified, then the code/software is synthesized. Software and hardware implementations may include code and circuitry configured to implement fixed-point and timing behavior (i.e., verify that a given system for which models have been created can perform within predefined limits, either under a predefined set of conditions, or over time). In fact, one can automatically generate code for embedded deployment and create test benches for system verification (e.g., using commercially or publicly available software, such as MATLAB® design software, available from Math-Works, located in Natick, Mass.).

Model-based design begins with building an architecture model from the system requirements. In one example, the system may be an insulin pump. A simulation/design model is then derived for the system. Typically, the simulation/design model is a relatively high-level, relatively low-fidelity model. However, it also includes code for the control loop(s) that will be running in the system (e.g., the insulin pump in its operating environment).

Initial system and integration tests are performed by simulating the high-level model under various conditions or sets of conditions to verify that the system is represented correctly and that it properly responds to input signals. Additional details may be added to the model, continuously testing and verifying the system-level behavior against the predefined limits of safe operation (e.g., specifications for the insulin pump performance). When the system is relatively complex (e.g., such as in a medical ventilator), models and code for individual components can be separately developed, and the individual components tested independently, and eventually tested in a full system simulation.

Ultimately, a detailed model of the system and the environment in which it operates is built. This model ideally captures accumulated knowledge about the system. Code may then be generated automatically from the model(s) of the control loop(s) in the system for software testing and verification in the actual physical system. Following such hardware-in-the-loop tests (e.g., using a prototype), the generated code may be downloaded onto a system controller for testing in an actual system. Software for generating, simulating and testing such model-based control systems may be commercially available (e.g., MATLAB® design software, available from MathWorks, Natick, Mass.).

One advantage of this approach is that iteration with a model is easier and faster than iterating with a particular source code implementation. In this approach, verified models may serve as a foundation for future secure controller design.

A second approach involves developing verified software safety monitors (implemented in a computer programming language, such as C, COBOL, BASIC, Fortran, ALGOL, Pascal, Prolog, VHDL, Verilog, and languages related thereto, such as C++) for integration into the control system software. In this approach, the main control loop for the system operates within a theorem-proven safety envelope for a set of critical parameters.

These approaches may be applied to both the systems themselves and a unit/component or subsystem thereof to calibrate such systems or component(s) thereof. A method of making a closed-loop control for a medical therapeutic system is summarized in FIG. 4.

Figure 4:
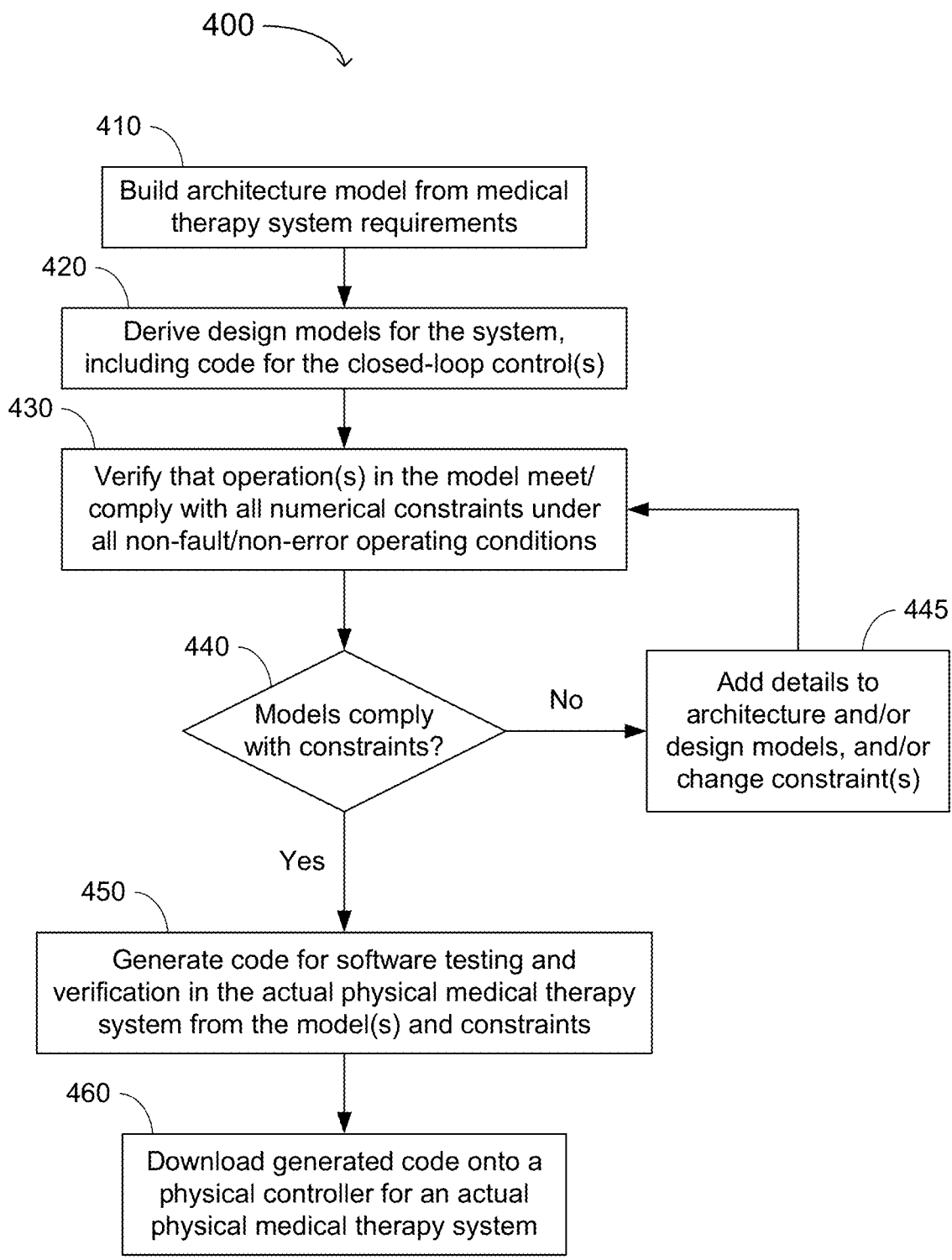
FIG. 4 summarizes an exemplary method of making a closed-loop control for a medical therapeutic system in accordance with one or more embodiments of the present invention.

FIG. 4 is a flow chart 400 for a method of making a closed-loop control for a medical therapy system. At 410, the method begins by building an architecture model from medical therapy system requirements. At 420, design models are derived for the system, including code for the closed-loop control(s), as described herein. At 430, the method comprises verifying that the operation or operations in the model meet or comply with all numerical constraints under all operating conditions that do not cause or result in a fault and/or an operating error.

At 440, the method determines whether the model or models comply with the constraints. In other words, the method determines whether all of the measurable and unmeasured parameters to be monitored in the system stay within the corresponding safety envelopes under the operating conditions being modeled.

If the model or models do not comply with the constraints and/or the parameters to be monitored do not stay within the safety envelopes, then the model is adjusted at 445. For example, details may be added to the architecture and/or design models, one or more of the constraints may be changed, or both. In some cases, the safety envelopes may be changed, typically to reduce the range of safe values for a given parameter. However, since the safety envelopes are typically fairly well-known for typical/conventional medical therapy systems, the safety envelopes are generally changed infrequently, or only when necessary (e.g., to obtain or maintain compliance with constraints and/or keeping operations within the safety envelopes).

If the model or models comply with the constraints and/or the parameters to be monitored stay within the safety envelopes, then code is generated from the model(s) and constraints at 450 for software testing and verification in the actual physical medical therapy system. Once the code is generated, it is downloaded onto a physical controller for an actual physical medical therapy system at 460. The physical medical therapy system is then operated, optionally under a variety of different operating conditions, to confirm that the physical medical therapy system can operate within the constraints, and the parameters of the physical medical therapy system being monitored stay within the corresponding safety envelopes.

Open-source, formal software tools are available for verification of embedded systems applications. Such tools include, for example, the Grackle symbolic execution tool and the open-source Copilot language for generating real-time C code and specifying and synthesizing distributed monitors, both of which are available from Galois Inc., Portland, Oreg.

The Grackle tool is a symbolic execution tool designed for symbolically executing MATLAB® and LLVM™ code, and evaluating those expressions using Boolean satisfiability problem (SAT) and satisfiability modulo theory (SMT) solvers such as ABC (an open-source created by the Berkeley Logic Synthesis and Verification Group at the University of California at Berkeley Department of Electrical Engineering and Computer Sciences, Berkeley, Calif.) and Yices (available from SRI International Computer Science Laboratory, Menlo Park, Calif.). The Grackle tool, for example, is intended to enable symbolic reasoning about numerical programs. It can be used to find inputs that may crash the system or that exceed physical tolerances, and it can integrate numerical and symbolic solvers in such analysis (e.g., code synthesis, execution and testing).

The Copilot tool is used to write embedded software monitors for relatively complex embedded systems, such as closed-loop controls for a medical ventilator system. However, it can also be used to develop a variety of functional embedded code (e.g., for programming and/or integration into a medical system controller). For instance, the Grackle tool can be used to reason and verify properties of MATLAB® models, and the Copilot tool can be used to synthesize run-time monitors (e.g., timing-based closed-loop control system models and code).

Practical techniques in control loop (or control subsystem) design, such as signal clamping, filtering, etc., may be included in the present method. When safety-critical models are verified, such verification expertise can guide generation and implementation of the code to make formal verification easier. This approach augments traditional testing methodologies, in that assertions about the software model can be made.

More specifically, the initial model for the medical therapeutic system is a mathematical description of the system. The initial model includes a core model for the behavior of system and/or its components, plus one or more (and typically a set or plurality of) constraints or mathematical limits on the system. For example, in an insulin pump, the core model will include a correlation between the distance that the plunger moves (or, equivalently, the number of rotations of the drive unit; see FIG. 2) and the number of units of insulin delivered to the patient. The core model and constraints can be written or created in MATLAB® software, Rust, etc.

In some embodiments, the constraints in the model for the medical therapeutic system are theorem-proven. This involves demonstrating, using theorem-proving tools (e.g., software, sometimes referred to as "theorem provers"), that the constraints maintain operation and/or performance of the medical therapeutic system within predetermined (and often or where possible, medically recognized) safety limits. When the core model and constraints are written or created in MATLAB® software or Rust, they are first converted to a theorem prover-compatible language, such as COQ, that can analyze and/or process state machines. To enable automated theorem proving, the constraints are expressly mathematically (e.g., a system parameter a does not exceed a value x; i.e., $\alpha \leq x$).

Running or executing the theorem prover on the model and constraints determines whether the constraints are theorem-proven or not. If the model stays within operational safety limits with the described constraints, the model and constraints is theorem-proven. If the model does not stay within operational safety limits with the described constraints (e.g., defined operational parameters that may or may not be monitored, such as input power level, concentration of therapeutic agent being delivered, etc.), then the constraints may be modified, the core model may be modified (e.g., to more closely match actual performance of an actual physical system or system component), or both. The theorem prover is run again on the modified model and/or constraint, and the determination as to whether the model stays within operational safety limits is made. This cycle is repeated until the model and constraints stay within the operational safety limits for the system. A theorem-proven model and safety envelope also has the advantage of protecting against software errors, and can result in a theoretically-trusted system. The control loop (including monitored parameter data/information from one or more sensors being fed back to the controller/core software) may be trusted, untrusted, or theorem-proven.

In an alternative embodiment, the model and constraints, once theorem-proven, can be converted into a different language, such as C or a C-compatible language, for deployment in the actual physical medical therapeutic system. A core controller executing or running theorem-proven control loops enables the use of untrusted user-interface systems (such as wireless systems, or Internet-based systems). From both a reliability perspective and a security perspective, the use of untrusted user-interface systems provides great flexibility in the selection of components for use in the medical therapy system and enables rapid deployment of new systems and software updates with confidence that they are unlikely to cause patient harm.

In embodiments that include a system controller, such as a microcontroller, microprocessor, field programmable gate array (FPGA) or application specific integrated circuit (ASIC), a daughterboard may be added (e.g., to a component or an operational subsystem) to provide a more sophisticated closed-loop control system. Intelligent software or code running on the daughterboard may make "recommendations" to the system controller, which stores the operational safety limits and determines system compliance with such limits. As used herein, a "recommendation" may be defined as data, information or an input sent to the controller (e.g., the core controller running the control loop, which may be theorem-proven) for updating a mode of operation in the medical therapy system. The controller may reject or ignore a recommendation when it is outside of the safety envelope.

Various aspects of the upper and/or lower limits (the "safety envelope") for a parameter to be monitored and/or controlled may be defined to ensure that the parameter to be monitored and/or controlled never exceeds an algebraic function of other parameters and/or values/measurements in the system. For example, in a medical ventilator system, a safety envelope for the peak inspiratory pressure (or PIP) of the patient can be defined mathematically as an upper bound of an algebraic function that specifies the patient's PIP based on gas flow rate(s), gas temperature, the patient's respiratory rate, etc. Another safety envelope in a medical ventilator system can be the minimum number of closed valves in the inspiratory pathway (i.e., components and conduits supplying a gas or gas mixture to a patient). Typically, the minimum number of closed valves is at least one. Yet another safety envelope in a medical ventilator system can ensure that a pressure increase in the system (e.g., as detected by a pressure sensor in the inspiratory pathway) indicative of a blocked airway results in an alarm signal (e.g., a flashing red light, a buzzer, bell or siren sound, etc.) being issued.

In particular, in the example of the medical ventilator system, the processor or microcontroller on the main printed circuit board (PCB) of the controller may be configured to execute a parameterized control loop (e.g., for each discrete component in the ventilator system to be controlled). For example, the number of operational states of the controller in the control loop may be strictly enumerable (e.g., a state diagram for the control loop has a specified or predetermined maximum number of states). In various embodiments, the states in the control loop may be limited to only those states that can be proven or demonstrated to be safe. The controller on any daughterboards that may be present, on the other hand, can run substantially any closed-loop control program or operation, and such daughterboards provide data and other information (e.g., in a form that can be characterized as device setting recommendations) to the processor or microcontroller on the main PCB of the controller. The controller may reject (e.g., not store or operate on) the data/information, or may modify the control loop on the daughterboard and/or the operation and/or setting(s) of the component, if the data or other information is outside the predefined safety envelope (e.g., upper and/or lower limits on a parameter affected by a component of the ventilator system).

Once implemented in a medical therapeutic system, the present closed-loop safety controls may cause the system controller to give a warning or issue an alert when one or more of the limits are exceeded, contravened or otherwise violated. For example, if a physician or other user of the medical therapeutic system attempts to command the system into an unsafe configuration, the present closed-loop safety controls may send an alert requiring an override in the system to be toggled.

An Exemplary Insulin Pump with Closed-Loop Control

Figure 2:
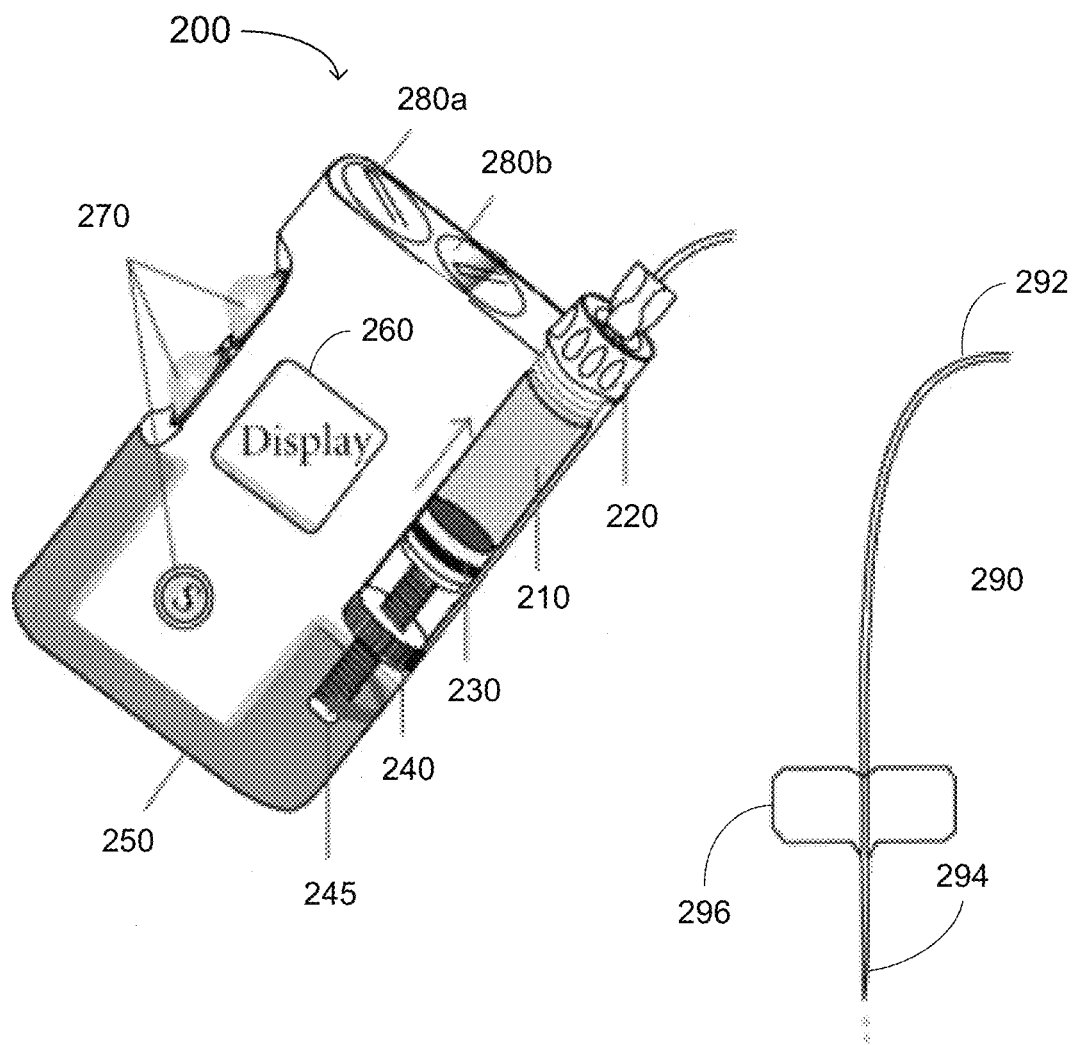
FIG. 2 is a diagram showing the physical components of a conventional insulin pump.

In an insulin pump, such as those exemplified in FIGS. 1-2, one may define certain constraints or limits for closed-loop control, such as the maximum deliverable amount of insulin per dose and/or per unit time. Such a control function may specify that the amount of insulin given to the patient in a given dose does not exceed a predetermined value x as a function of patient estimations of carbohydrate intake, the patient's body weight, the patient's sensitivity to insulin, and/or one or more glucose sensor readings or measurements. Different control functions and different constraints or limits may exist for the same patient using the same pump, depending on whether the dose is a bolus dose or a basal or background dose.

In one example of the use of closed-loop safety control in an insulin pump, the controller in the insulin pump can receive and execute an operational function from the core model and constraints generated according to the flow chart in FIG. 4. For example, one such operational function can specify that the insulin pump delivers no more than x units of insulin when a first or second derivative of the level of glucose in the patient (e.g., as a function of time) exceeds a threshold value y (e.g., in mg/dl/unit time). Other constraints or limits for closed-loop control in an insulin pump can ensure that an alarm is triggered if an anticipated response is not observed, such as observation of an indicator of a healed-over injection site or a faulty sugar monitor.

In some embodiments of the invention, the core controller runs theorem-proven code with a defined safety envelope, and an external system makes recommended updates (i.e. recommendations) to the operational mode of the system as defined by the code and executed by the core controller. The "core" systems include (1) the core controller, which generally comprises a PCB with a microcontroller/processor, traces configured to transfer signals to control processes and/or components of the system and receive signals from sensors and the user interface, and electronic signal modifiers (e.g., buffers, capacitors, resistors, inverters, etc., electrically connected to the traces) thereon, and (2) core software, derived from a system architecture model and code for the closed-loop control(s) (see, e.g., FIG. 4), running on the core controller. In preferred embodiments, the core software is theorem-proven and does not permit operation(s) outside of the safety envelope (which is based on constraints in the closed-loop control[s]). Any attempt to change a parameter in the system, the operational mode of the system, or any of the constraints (e.g., as a result of feedback from a sensor, input from a user, etc.) is in the form of a recommendation to the core controller, which may disregard the recommendation if it (or its operational result) is outside of at least one safety envelope.

An Exemplary Ventilator with Closed-Loop Control

Figure 3:
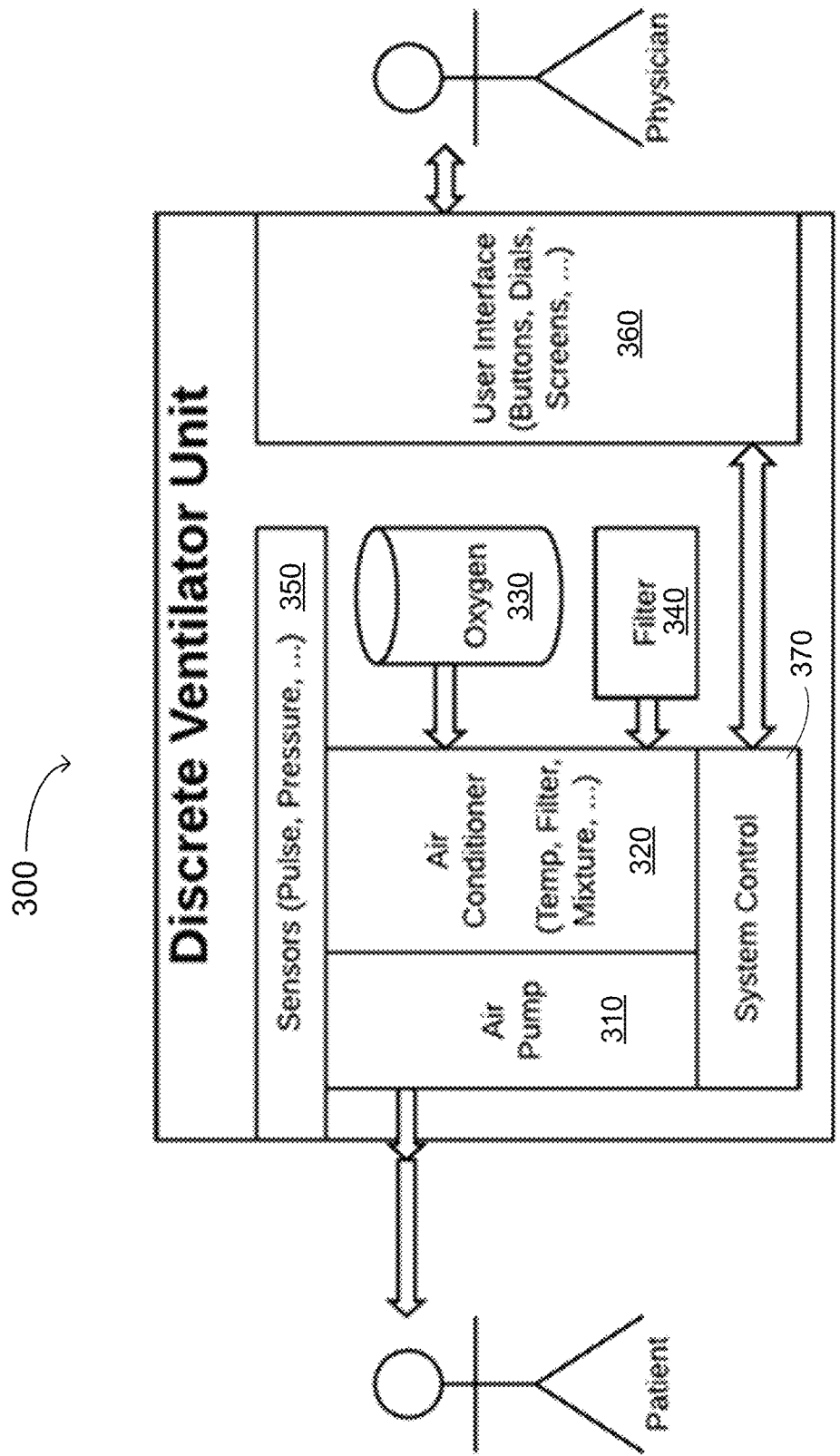
FIG. 3 is a diagram showing a conventional medical ventilator system.

In a medical ventilator system (see, e.g., FIG. 3), the core controller providing the system control function accepts inputs from other processes, such as the air conditioner, the air pump, the sensors, and the user interface, and sends commands to various components therein, such as the air pump, valves controlling the flow of air and oxygen to the air conditioner and from the air conditioner to the patient, and the sensors, and sends information to a display in the user interface. The inputs from the other processes may be deterministic inputs that function as recommendations (e.g., recommended settings for the pump, one or more of the valves, the heater and/or humidifier in the air conditioner, etc.). In some examples, the inputs are received by a separate processor (e.g., in a computer that functions as the user interface, in combination with a computer monitor that functions as the display), which then accepts the values and transmits the corresponding information to the core controller in the system control block. The system control may reject the recommendation if it results in any of the safety envelopes being exceeded or violated. However, in some cases, a physician or other user (e.g., having appropriate authorization) may override the exceeded or violated safety envelope through the user interface.

When the process (or a parameter associated with the process) exceeds the safety envelope (i.e., constraints on the process within which the system is known to operate safely), the core controller will reject the information (e.g., identify it as a violation) and either automatically change a setting or value in the process to bring the process or parameter within the safety envelope or prompt a user to manually enter a value for the parameter to bring the process or parameter within the safety envelope. In some cases, the user may be prompted to manually enter a new value for the constraint. Optionally, the core controller accepts the manually-entered constraint value when it is within the safety envelope.

For example, when there is a temperature deviation (e.g., the temperature of the air delivered from the air conditioner is too high, as measured by a temperature sensor at the output of the air conditioner), the volume of gas delivered to the patient may vary outside the safety envelope (e.g., may exceed an upper limit in the control loop). However, it may not be possible to directly measure the volume of air or other gas delivered to the patient. In such a system, when the volume of air or other gas delivered to the patient is under closed-loop control (e.g., for safety reasons), the volume of air or other gas can be controlled within the safety envelope by controlling the pressure of the air or other gas in the system. The pressure sensor is at a known point in the system, where the relationship between the pressure at that point and the temperature of the gas in the air conditioner provide a known or determinable volume of gas to the patient. Such a system is valuable because it may not be easy to quickly adjust the parameter that is outside the safety constraint(s).

Figure 5:
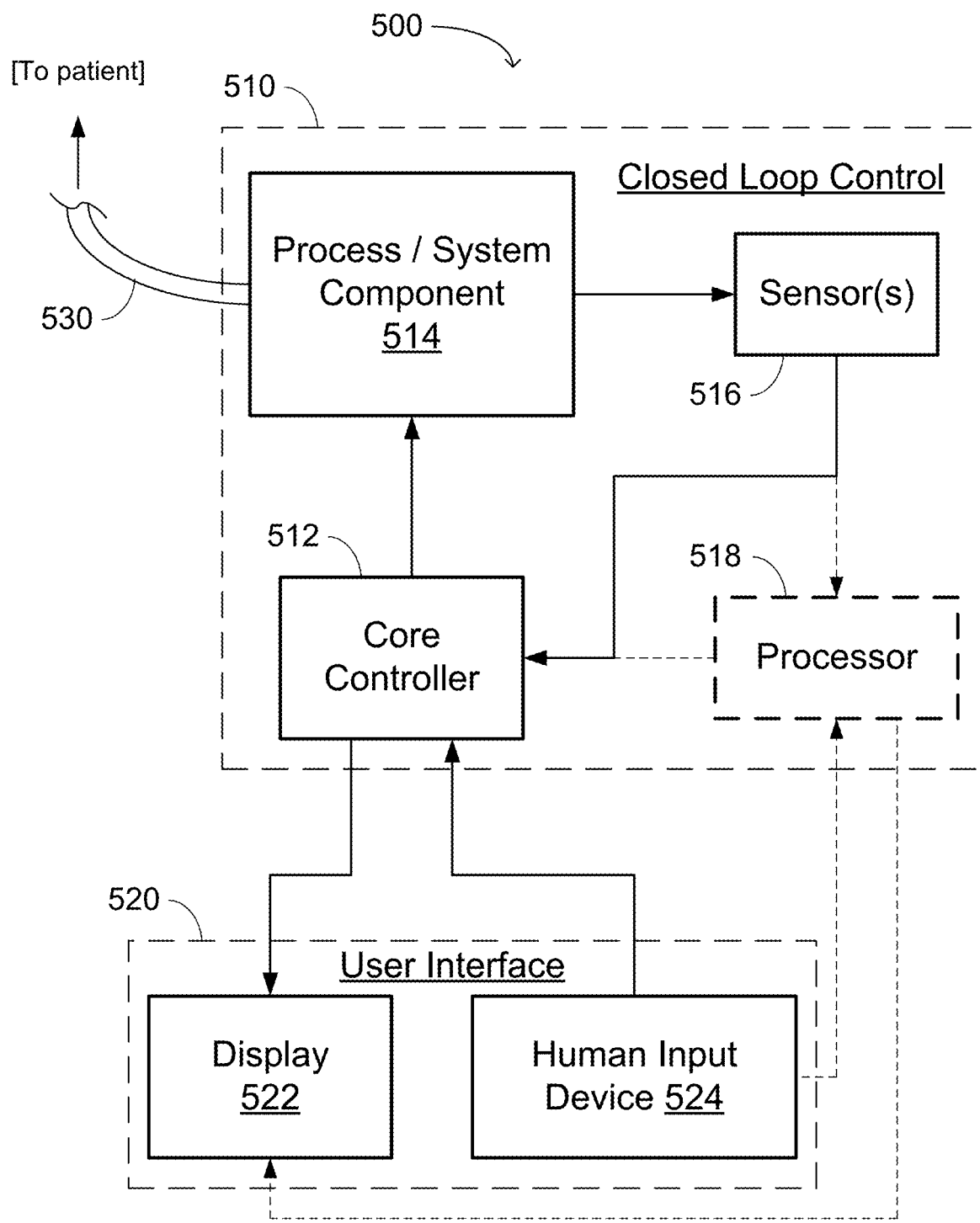
FIG. 5 is a diagram of an exemplary closed-loop control subsystem for a medical therapy system, according to embodiments of the present invention.

Thus, medical consequences of a certain setting or combination of settings in a medical therapeutic system can be controlled with a closed loop. Referring to FIG. 5, a closed loop control subsystem 510 may comprise the core controller 512, a process or system component 514 controlled by the core controller 512, one or more sensors 516 monitoring a corresponding number of parameter values, and optionally a processor 518 (e.g., in a computer configured to provide information to a display 522 and receive information from a human input device 524, such as a keyboard, mouse, or touchscreen). The solid arrows indicate a path for communicating information (e.g., a bus or wire carrying data thereon) and the direction of information flow. The dashed arrows indicate path for communicating information to or from the optional processor 518. The medical consequences of the setting or combination of settings in the process or system component 514 may not be knowable to the closed-loop control software operating in the core controller 512, but the sensor readings/measurements are, and a determination as to whether the process or system component 514 is operating within the safety envelope can easily be made by the closed-loop control software based on the sensor readings/measurements.

Other examples of closed-loop control subsystems in the medical ventilator may be based on user inputs. For example, a physician or nurse may set the lower and upper limits for the respiratory rate of a patient receiving gas from a ventilator at 20-60 breaths per minute and the minimum and maximum limits for the tidal volume at 4-6 liters/min. From these user inputs (plus other parametric data from the ventilator system) and the system model description in the control software (generated in accordance with the flow chart in FIG. 4) programmed and/or embedded in the core controller 514, the core controller 514 can calculate a gas flow rate for the ventilator that provides the gas within the user-defined safety envelope. The gas flow rate may be calculated from parameters such as opening and closing times of gas valves in the ventilator, the Cv of the valve(s) or the flow rate of the gas through the valve(s), and the pressure(s) at one or more points or locations in the ventilator, among other actual or potential inputs.

The present closed-loop control subsystems can also calculate target parameter values for monitoring by the closed-loop control subsystem. For example, the closed-loop controls in the core controller of the ventilator may have a function call to open or close a valve, or to set a valve flow rate. The closed-loop control software in the core controller then executes in its main loop instructions to receive the patient respiratory rate (which may be determined and input by the user) and the target tidal volume (i.e., volume of air or gas inspired by the patient per breath, which may also be determined and input by the user), and to calculate or determine the inspiration period (i.e., the length of time for the patient to receive air or gas from the ventilator). The core controller then sets the target flow rate or valve open time (i.e., knowing the fixed flow rate of the valve) to provide a volume of air equal to the tidal volume times the inspiration period. The safety envelope is already input into the closed-loop control subsystem. The main loop instructions may be run on a separate computer in communication with the core controller, in some systems.

Thereafter, the valve open time or valve flow rate may be monitored by the closed-loop control system (e.g., in response to pressure readings before and after the valve, which may be taken periodically to determine or calculate corresponding changes in gas volume per unit time). The control loop for the valve open time or valve flow rate makes periodic calls to determine the valve open time or valve flow rate (e.g., every 0.1-10 sec). The pressure readings are generally taken at a rate at least as frequent as the calls to determine the valve open time or valve flow rate. If the values of the valve open time or valve flow rate are always within the safety envelope (e.g., for a minimum length of time, such as 10 minutes, 1 hour, etc., and/or after all of the control loops in the core controller converge and/or are stably within the safety envelopes for the process or parameter being controlled), then the target value(s), the safety envelope(s), and the closed-loop control subsystem are theorem-proven.

Furthermore, when used in an insulin pump, for example, the present closed-loop controller can be programmed with a variable target parameter (e.g., blood glucose level as a function of the time of day; the blood glucose level of typical, healthy patients varies throughout the day, oftentimes relatively predictably). However, the present closed-loop controls and/or one or more of the targets therefor may or may not fall within the constraints in the core controller. Theorem-proven closed-loop controls, in effect, generally maintain the medical therapy system within known safe bounds or constraints. The core software may function as a kind of "guardian" for the safe operation of the system. As a result, it may be updated relatively infrequently (e.g., once per month, once per year, etc.). On the other hand, untrusted closed-loop controls (e.g., based on one or more recommendations), which are not theorem-proven, may be updated relatively frequently, because the system is provably safe in the absence of malicious input when running theorem-proven core software, and such updates may improve the quality of patient care.

CONCLUSION

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. A medical therapeutic system, comprising:
    a) one or more medical therapeutic system components configured to deliver at least one of a controlled amount of a substance, energy, or force to a patient;
    b) a theorem-proven controller configured and formally verified such that any and all operating instructions provided by the controller to the one or more components do not produce a result outside a corresponding predefined safety envelope; and
    c) one or more sensors, each configured to:
        i) measure or determine a value of a measurable parameter (1) of the one or more components and/or (2) caused by an operation of the one or more components, and
        ii) provide information corresponding to the value of the measurable parameter to the controller,
    wherein the predefined safety envelope corresponds to known safe values of the measurable parameter or an unmeasured parameter based on the measurable parameter.

2. The system of claim 1, wherein the controller includes a physical memory containing non-transitory, executable code defining, at least in part, a function that describes mathematically the corresponding operation of the one or more components, and includes a model of the corresponding operation of the one or more components, and wherein the predefined safety envelope includes one or more mathematical descriptions of maximum or minimum limits for the measurable parameter or the unmeasured parameter.

3. The system of claim 2, wherein the predefined safety envelope comprises mathematical descriptions of the maximum limit and the minimum limit for the unmeasured parameter.

4. The system of claim 1, wherein the one or more components comprise first and second components, the controller includes a physical memory containing non-transitory, executable code defining, at least in part, a function that describes mathematically the corresponding operation of the one or more components, and wherein the predefined safety envelope includes one or more mathematical descriptions of maximum and/or minimum limits for the measurable parameter or the unmeasured parameter.

5. The system of claim 1, wherein the one or more components comprise first and second components, the one or more sensors comprise first and second sensors, and the controller is configured to determine whether operations of each of the first and second components are within corresponding first and second predefined safety envelopes according to first and second functions that respectively describe mathematically the corresponding operations of the first and second components.

6. The system of claim 1, wherein each of the one or more components is configured to provide to the controller a recommendation relating to the operation, and the controller is configured to (a) accept the recommendation when the operation of the one or more components is within the corresponding predefined safety envelope, and (b) necessarily reject the recommendation when the operation of the one or more components is outside the corresponding predefined safety envelope.

7. The system of claim 1, wherein the controller is configured to determine whether the operation of the one or more components is within the corresponding predefined safety envelope by calculating a value of an unmeasured parameter (1) of the one or more components and/or (2) caused by the operation of the one or more components from the value of the measurable parameter.

8. The system of claim 1, further comprising:
    a) a reservoir, chamber or vessel containing the substance; and
    b) a tube, conduit or other delivery mechanism through which the substance is delivered to the patient.

9. The method of claim 1, wherein providing information corresponding to the value of the measurable parameter to the controller includes providing the information directly to the controller.

10. A theorem-proven controller for a medical therapeutic system, comprising:
    a) a theorem-proven microcontroller, microprocessor, field programmable gate array (FPGA), or application specific integrated circuit (ASIC) configured to execute instructions to determine whether one or more operations of one or more components of the medical therapeutic system are within a corresponding predefined safety envelope according to one or more functions, each of which corresponds to a unique one of the one or more operations, that describes mathematically the corresponding operation; and
    b) a physical memory containing non-transitory, executable code including the instructions, the function that describes mathematically the corresponding operation of the one or more components, and the predefined safety envelope, wherein:
        the function that describes mathematically the corresponding operation of the one or more components includes a model of the corresponding operation of the one or more components,
        the predefined safety envelope comprises one or more mathematical descriptions of maximum and/or minimum limits for a measurable parameter of the one or more components and/or a value corresponding to the measurable parameter, and/or a value caused by the operation of the one or more components,
        the theorem-proven microcontroller, microprocessor, FPGA or ASIC is configured and formally verified such that (i) any and all operating instructions provided to the one or more components are within the corresponding safety envelope or (ii) an alert is provided to a user of the medical therapeutic system in response to at least one of the one or more operations of the one or more components being outside the corresponding safety envelope.

11. A method of generating a closed-loop control for a medical therapy system, comprising:
    a) building an architecture model from requirements for the medical therapy system;
    b) deriving (i) design models for the medical therapy system and/or for processes or components thereof and (ii) a function that describes mathematically one or more operations of the medical therapy system, the process(es), or the component(s), wherein the function includes one or more measurable parameters (1) of the system, process(es), or component(s) and/or (2) caused by the operation(s);

c) adding or inputting one or more control loops to the architecture and design models configured to determine whether the operation(s), the process(es) or the component(s) are within a corresponding predefined safety envelope according to the function;

d) determining whether the models comply with predefined constraints for the system, the process(es), or the component(s) based on the function and the safety envelope(s);

e) when at least one of the one or more operations of the system, the process(es), or the component(s) is outside the predefined safety envelope, modifying one or more of the architecture and/or design models and/or one or more of the constraints and determining again after modification whether the models comply with the constraints; and f) downloading, installing, or embedding code generated from the architecture and/or design models, the safety envelope(s) and the constraints onto or in a controller in the medical therapy system.

12. The method of claim 11, further comprising, after simulating the models under the constraints, determining that all of the operation(s) of the system, the process(es), or the component(s) are within the corresponding predefined safety envelope.

13. The method of claim 12, wherein the code is downloaded, installed, or embedded onto or in the controller after determining that all of the operation(s) of the system, the process(es), or the component(s) are within the corresponding predefined safety envelope.

14. The method of claim 11, wherein the predefined safety envelope comprises one or more mathematical descriptions of maximum or minimum limits for a measurable parameter or an unmeasured parameter of and/or affected by the operation(s) of the process(es) or component(s).

15. The method of claim 14, wherein the predefined safety envelope comprises mathematical descriptions of the maximum limit and the minimum limit for the unmeasured parameter.

16. The method of claim 11, wherein the system or the processes or components comprise first and second processes or components, and the controller determines whether the operations of each of the first and second processes or components are within corresponding first and second predefined safety envelopes according to first and second functions that respectively describe mathematically the corresponding operations of the first and second processes or components.

17. The method of claim 11, wherein each of the process(es) or component(s) are configured to provide a recommendation relating to the corresponding operation(s), and the model accepts the recommendation when the corresponding operation(s) of the process(es) or component(s) are within the corresponding predefined safety envelope, but the model necessarily rejects the recommendation when at least one of the corresponding operation(s) of the process(es) or component(s) is outside the corresponding predefined safety envelope.

18. The method of claim 17, wherein the code generated from the architecture and/or design models is theorem-proven, and the control loop(s) are untrusted.

19. The method of claim 11, wherein determining whether the models comply with the predefined constraints comprises:

a) calculating a value of an unmeasured parameter (1) of the process(es) or component(s) and/or (2) caused by the operation(s) of the process(es) or component(s), from one or more values of a corresponding measurable parameter; and b) comparing the value of the unmeasured parameter with the corresponding safety envelope.

* * * * *